(12) United States Patent
Henning et al.

(10) Patent No.: US 12,397,142 B2
(45) Date of Patent: Aug. 26, 2025

(54) MICRONEEDLE ARRAY HAVING AN ACTIVE INGREDIENT IN THE FORM OF SALTS

(71) Applicant: LTS LOHMANN THERAPIE-SYSTEME AG, Andernach (DE)

(72) Inventors: Andreas Henning, Meßstetten (DE); Thomas Hille, Neuwied (DE); Gabriel Wauer, Ahrweiler (DE); Heiko Spilgies, Berlin (DE); Rolf Pracht, Höhr-Grenzhausen (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 384 days.

(21) Appl. No.: 16/771,586

(22) PCT Filed: Dec. 14, 2018

(86) PCT No.: PCT/EP2018/085083
§ 371 (c)(1),
(2) Date: Jun. 10, 2020

(87) PCT Pub. No.: WO2019/115815
PCT Pub. Date: Jun. 20, 2019

(65) Prior Publication Data
US 2020/0297985 A1   Sep. 24, 2020

(30) Foreign Application Priority Data

Dec. 14, 2017 (DE) .................. 10 2017 130057.0

(51) Int. Cl.
| | |
|---|---|
| *A61M 37/00* | (2006.01) |
| *A61K 9/00* | (2006.01) |
| *A61K 31/485* | (2006.01) |
| *A61K 47/32* | (2006.01) |
| *A61K 47/34* | (2017.01) |

(52) U.S. Cl.
CPC ....... *A61M 37/0015* (2013.01); *A61K 9/0021* (2013.01); *A61K 31/485* (2013.01); *A61K 47/32* (2013.01); *A61K 47/34* (2013.01); *A61M 2037/0023* (2013.01)

(58) Field of Classification Search
None
See application file for complete search history.

(56) References Cited

U.S. PATENT DOCUMENTS

| | | | | |
|---|---|---|---|---|
| 7,156,838 B2 * | 1/2007 | Gabel | ........... | A61M 5/14248 604/173 |
| 9,017,289 B2 * | 4/2015 | Backes | ........... | A61M 37/0015 604/173 |
| 9,149,442 B2 | 10/2015 | Maier | | |
| 11,547,676 B2 * | 1/2023 | Jain | ........... | A61K 9/7053 |
| 2005/0226922 A1 | 10/2005 | Ameri et al. | | |
| 2007/0081977 A1 | 4/2007 | Horstmann | | |
| 2008/0008745 A1 * | 1/2008 | Stinchcomb | ........ | A61K 31/4355 424/443 |
| 2008/0183144 A1 | 7/2008 | Trautma et al. | | |
| 2009/0182306 A1 * | 7/2009 | Lee | ........... | B29C 41/04 604/506 |
| 2013/0273119 A1 | 10/2013 | Engqvist et al. | | |
| 2016/0082241 A1 | 3/2016 | Burton et al. | | |
| 2016/0271380 A1 * | 9/2016 | Poon | ........... | A61M 37/0015 |
| 2018/0099133 A1 | 4/2018 | Heuser et al. | | |
| 2018/0193256 A1 | 7/2018 | Kabata et al. | | |

FOREIGN PATENT DOCUMENTS

| | | |
|---|---|---|
| CN | 101612141 A | 12/2009 |
| CN | 102406640 A | 4/2012 |
| CN | 105283216 A | 1/2016 |
| DE | 10353629 A1 | 6/2005 |
| DE | 102007041557 B4 | 3/2011 |
| JP | 2007-532645 A | 11/2007 |
| JP | 2010-516337 A | 5/2010 |
| JP | 2013-032324 A | 2/2013 |
| JP | 2013-536875 A | 9/2013 |
| JP | 2017-051312 A | 3/2017 |
| WO | WO-2008091602 A2 | 7/2008 |
| WO | 2014/193729 A1 | 12/2014 |
| WO | WO-2014191979 A1 | 12/2014 |
| WO | 2016/142705 A1 | 9/2016 |

(Continued)

OTHER PUBLICATIONS

McCrudden et al., Design and physicochemical characterisation of novel dissolving polymeric microneddle arrays for transdermal delivery delivery of high dose, low molecular weight drugs. Journal of controlled release, 180:71-80. (Year: 2014).*
International Preliminary Examination Report for PCT/EP2018/085083 mailed Apr. 2, 2020.
International Search Report for PCT/EP2018/085083 mailed Apr. 17, 2019.
International Preliminary Report on Patentability Chapter II received for PCT Patent Application No. PCT/EP18/085083, mailed on Apr. 2, 2020, 17 pages (6 pages of English Translation and 11 pages of Original Document).
Cao et al., "Development of sinomenine hydrochloride-loaded polyvinylalcohol/maltose microneedle for transdermal delivery," Journal of Drug Delivery Science and Technology, vol. 35, Oct. 2016, pp. 1-7.

*Primary Examiner* — Lakshmi S Channavajjala
(74) *Attorney, Agent, or Firm* — Faegre Drinker Biddle & Reath LLP

(57) ABSTRACT

The invention relates to a microneedle array, in particular to an applicator system, and to the use thereof for the intradermal delivery of active ingredients in the form of salts, in particular medicinal drugs in the form of salts, wherein this microneedle array is suitable for penetrating the skin of humans or animals, and the microneedles are made of a formulation, containing at least one active ingredient in the form of a salt and at least one biodegradable polymer.

15 Claims, No Drawings

(56) References Cited

FOREIGN PATENT DOCUMENTS

| | | |
|---|---|---|
| WO | WO-2016162449 A1 | 10/2016 |
| WO | WO-2017043517 A1 | 3/2017 |

\* cited by examiner

MICRONEEDLE ARRAY HAVING AN ACTIVE INGREDIENT IN THE FORM OF SALTS

CROSS-REFERENCE TO RELATED APPLICATIONS

This application is a national stage application (under 35 U.S.C. § 371) of PCT/EP2018/085083, filed Dec. 14, 2018, which claims benefit of German Application No. 10 2017 130057.0, filed Dec. 14, 2017, both of which are incorporated herein by reference in their entirety.

The invention relates to a microneedle array, in particular to an applicator system, and to the use thereof for the intradermal delivery of active ingredients in the form of salts, in particular medicinal drugs in the form of salts, wherein this microneedle array is suitable for penetrating the skin of humans or animals, and the microneedles are made of a formulation, containing at least one active ingredient in the form of a salt and at least one biodegradable polymer.

Microneedle systems and devices in which microneedle arrays are used for the painless intradermal (or transdermal) administration of active ingredients, and in particular of medicinal drugs, are known from the prior art. The transdermal delivery of active ingredients in the form of salts is disclosed in DE 102007041557 B4, by the applicant, for a patch or transdermal therapeutic system (TTS).

The skin consists of several layers. The outermost layer of the skin, this being the stratum corneum, has known blocking properties to prevent foreign substances from penetrating into the body and the body's own substances from exiting the body. The stratum corneum, which is a complex structure composed of compacted horny cell residues having a thickness of approximately 10 to 30 micrometers, forms a watertight membrane for this purpose to protect the body. This natural impermeability of the stratum corneum prevents most pharmaceutical agents and other substances from being administered through the skin as part of an intradermal delivery.

As a result, various substances are therefore administered, for example, by generating micropores or cuts in the stratum corneum and feeding or delivering a medicinal drug into or beneath the stratum corneum. In this way, it is also possible to administer a number of medicinal drugs subcutaneously or intradermally or intracutaneously, for example.

It remains a problem in the prior art that an active ingredient can usually be delivered in the form of the base thereof; however, this form is less stable than the salt form thereof, which consequently results in losses. A high need consequently exists to provide the active ingredients to be delivered in the form of salts in a suitable pharmaceutical form.

It is therefore the objective object of the invention to provide a suitable pharmaceutical form for the intradermal delivery of active ingredients in the form of salts.

The object is achieved by the conveyed technical teaching of the claims.

The invention thus relates to such a teaching having the features of claim 1, this being a microneedle array for use with the intradermal delivery of an active ingredient in the form of a salt, comprising a plurality of microneedles on a carrier, wherein the microneedles are composed of a formulation, containing at least one active ingredient in the form of a salt and at least one biodegradable polymer.

It is particularly advantageous that the penetrated microneedles dissolve in-situ and directly resorb in the skin. This eliminates the need for the microneedles to be hollow on the inside or to comprise a channel, since the active ingredient in the form of salts is introduced into the skin by being embedded in a formulation. The formulation dissolves in the body, and the active ingredient in the form of salts is released. Hollow microneedles furthermore have the disadvantage that the cavities can become clogged with coagulating blood during the wearing period.

According to the invention, all appropriate active ingredients in the form of salts that suitable for intradermal delivery are covered.

The active ingredient in the form of salts is preferably an active ingredient from the group of analgesics, such as narcotics. Morphine derivatives, heroin and buprenorphine, or fentanyl and the derivatives thereof, sufentanil and alfentanil, shall be mentioned as preferred substances, however all of them in the form of the salts thereof. Without limiting the invention, in particular fentanyl citrate or buprenorphine hydrochloride shall be understood as salts according to the invention. The invention likewise encompasses other known opioid salts, such as oxycodone hydrochloride or morphine hydrochloride. It is preferred that the salts are soluble in a pharmaceutically acceptable solvent, such as ethanol. The term "soluble" shall mean that 1 part of the salt dissolves in 10 to 30 parts of the solvent.

A person skilled in the art is able to produce salts corresponding to the active ingredients.

The microneedle array can comprise a plurality of microneedles so as to be able to release an active ingredient in the form of a salt via the skin or into the skin of a patient, wherein the microneedle array is applied to the skin of the patient. Each of the microneedles of the microneedle array preferably comprises an elongated shaft having two ends, the one end of the shaft forming the base of the microneedle by way of which the microneedle is attached to the planar carrier or by way of which the microneedle is integrated into the planar carrier. The end of the shaft located opposite the base preferably has a tapered shape so as to enable the microneedle to penetrate into the skin as easily as possible.

The microneedle array according to the invention is suitable for use with the intradermal delivery of an active ingredient in the form of a salt and comprises a plurality of microneedles on a carrier, wherein the microneedles comprise a formulation or are composed of a formulation, containing at least one active ingredient in the form of a salt and at least one biodegradable polymer.

Particularly preferably, the biodegradable polymers can be water-soluble polymers, and preferably those polymers selected from the group consisting of polyvinylpyrrolidone, polyvinyl alcohols, cellulose, dextrans, alpha-hydroxy acids, such as lactic acid and/or glycolic acid, polylactides, polyglycolides, polylactide-co-glycolides, and copolymers thereof with polyethylene glycol, polyanhydrides, poly(ortho)esters, polyurethanes, polybutyric acids, polyvaleric acids, and polylactide-co-caprolactones.

Within the meaning of the present invention, polymers that dissolve up to 50% in water or ethanol or alcohol/water mixtures at room temperature, or up to 80% in boiling heat, that is, at approximately 78° C., are also considered to be water-soluble.

The microneedles can comprise a shaft having a round cross-section or a non-round cross-section, for example having a triangular, quadrangular or polygonal cross-section. The shaft can have one passage or multiple passages, extending from the needle base to the needle tip or approximately to the needle tip. The microneedles can be designed as (barbed) hooks, wherein one or more of these microneedles comprise one or more such hooks. Furthermore, the microneedles can be configured in a helical shape and be rotatably disposed and thereby, when a rotating motion is applied, facilitate the penetration into the skin and effectuate anchoring in the skin (DE 103 53 629 A1), in particular at the desired penetration depth in the epidermis.

The diameter of a microneedle typically ranges between 1 μm and 1000 μm, and preferably between 10 μm and 100 μm. The diameter of a passage typically ranges between 3 μm and 80 μm and is suitable for preferably liquid substances, solutions and substance preparations to pass through. The length a microneedle typically ranges between 5 μm and 6,000 μm, and in particular between 100 μm and 700 μm.

The microneedles are attached at the base thereof to a planar carrier or are integrated into a planar carrier. The microneedles are preferably disposed so as to be situated substantially perpendicularly to the surface area of the carrier. The microneedles can be arranged regularly or irregularly. An arrangement of multiple microneedles can comprise microneedles having differing cross-sectional shapes, differently dimensioned diameters and/or differing lengths. The arrangement can likewise comprise solid microneedles as well as semi-solid composites.

The density of the microneedles on a carrier can be 5 to 5,000 pieces/cm$^2$, and in particular 5 to 1000 pieces/cm$^2$.

The microneedle array can comprise a planar carrier, wherein the carrier essentially has a disk-shaped, plate-shaped or film-shaped basic shape. The carrier can have a round, an oval, a triangular, a quadrangular or a polygonal base surface area. The carrier can be produced from a variety of materials, such as a metal, a ceramic material, a semiconductor, an organic material, a polymer or a composite. Materials suitable for producing the carrier can preferably be films or web-shaped materials, for example microporous membranes, preferably made of polyethylene (PE) or polypropylene (PP), or diffusion membranes, preferably made of ethylene-vinyl acetate copolymer (EVA) or polyurethane (PUR). Suitable materials for producing the carrier can be selected from the group consisting of polyesters, such as polyethylene terephthalates (PET), polycarbonates (PC), polyether ketones (PAEK), polyethylene naphthalate (PEN), polybutylene terephthalates (PBT), polyurethanes (PU), polystyrenes (PS), polyamides (PA), polyoxymethylene (POM), polyolefins such as polyethylene (PE) and polypropylene (PP), polytetrafluoroethylene (PTFE), polyvinyl chloride (PVC), polyvinylidene chloride (PVDC), polylactate (PLA), polymethyl methacrylate (PMMA) and cellulose-based plastic materials, such as cellulose hydrate or cellulose acetate. Suitable materials for producing the carrier can also be selected from the group of metals, which include aluminum, iron, copper, gold, silver, platinum, alloys of the aforementioned metals, and other pharmaceutically acceptable metal foils or metallized films.

The carrier is preferably made of a flexible material, for example a plastic material. A carrier made of a flexible material can better conform to the surface of the skin and the curvature thereof than a carrier made of a non-flexible material. In this way, better contact between the microneedle array and the skin is achieved, thereby improving the reliability of the microneedle array.

In a preferred embodiment, the microneedle array is a flat or planar microneedle array.

In another embodiment of the invention, applicator systems can be used to place a microneedle array onto the skin under pressure and result in a sudden burden on the skin. In another preferred embodiment, the microneedle system comprising a microneedle array is configured with an applicator. Such applicators advantageously allow a pressure mechanism to be activated for the microneedle array to penetrate the skin or stratum corneum (see, for example, WO2008091602A2, WO2016162449A1).

In a further embodiment, the applicator system comprising a microneedle array can be configured with customary functional objects that allow fixation on the skin as well as easy handling for exerting pressure onto the skin and that can comprise, in particular, at least one fixation means.

Within the scope of the present invention, an applicator system is a system comprising a device that causes the microneedle array for administering the active ingredient in the form of a salt to be provided on the skin, and the active ingredient in the form of a salt to be intradermally delivered.

In a preferred embodiment, the applicator system can comprise a trigger device, which is electrically or mechanically controlled. For example, the applicator system can comprise a plunger, which places or applies the microneedle array onto the skin, so that the microneedles penetrate the skin.

The trigger device can comprise a pump, a syringe or a spring, for example, whereby a push of the plunger can be carried out with sufficient energy. The plunger can be of any arbitrary shape and nature and is to primarily achieve that the microneedle array is provided from a first position into a second position for administering the active ingredients onto the skin.

The applicator system can furthermore comprise a push button or a thread.

According to a further embodiment, the microneedle array can comprise fixation means that are preferably attached to the skin of a patient or test subject by way of a contact adhesive strip or patch, also referred to as a needle patch. Suitable contact adhesives include high viscosity substances that adhere to the skin after briefly applying minor pressure, known as pressure-sensitive adhesives (PSA). These have high cohesion and adhesion forces. It is possible, for example, to use poly(meth)acrylate-based, polyisobutylene-based or silicone-based contact adhesives. In a further embodiment, the fixation means can be made up of a band, an elastic band, rubber or strap. Secure fastening to the body can be achieved by way of such fixation means.

The invention thus likewise relates to an applicator system according to the invention comprising a microneedle array or to a microneedle array for intradermal delivery, which comprises fixation means for the skin.

According to the invention, the term "intradermal delivery" (synonym: "intracutaneous delivery") describes the administration of arbitrary active ingredients via the microneedle array into the skin and requires the microneedles to pierce or penetrate the skin.

The invention thus likewise relates to a method for intradermal delivery, wherein a microneedle array comprising a plurality of microneedles on a carrier is applied, in particular, by way of an applicator system, wherein the microneedles are made of a formulation, containing at least one active ingredient in the form of a salt and at least one biodegradable polymer.

The invention further relates to the use of a microneedle array comprising a plurality of microneedles on a carrier, and in particular a corresponding applicator system, wherein the microneedles are made of a formulation containing at least one active ingredient in the form of a salt and at least one biodegradable polymer.

The following examples are provided to further describe the invention, without limiting the invention to these examples.

EXAMPLE 1

100 mg fentanyl citrate, 6.9 g Resomer R 202 H (polylactide, PDLLA) and approximately 3 g ethanol are dissolved in boiling heat. While still in the hot state, this solution is printed, using a 3D printer, on circular polyethylene terephthalate film pieces having a thickness of 15 µm and a surface area of 2.5 cm$^2$ in such a way that, after cooling, needles having a height of approximately 0.4 to 0.8 mm result. These needles are composed of 1.43% fentanyl citrate and 98.57% Resomer R 202 H, and still contain traces of ethanol. The printer is set in such a way that approximately 20.7 mg, containing 0.3 mg fentanyl acetate, is obtained after the solvent has evaporated. 0.3 mg fentanyl citrate corresponds to the initial daily dose for transdermal pain management. The PET film is placed, with the side facing away from the needles, on mesh coated with contact adhesive, so that the adhesive mesh protrudes over the needle patch. The needle patch and the contact adhesive mesh are covered for storage with a thermoforming sheet made of siliconized HDPE film, 175 µm, so as to protect the polymer needles. For the delivery, the thermoformed film is pulled off. The needle patch is attached to a patient suffering from pain and fixed by way of the adhesive layer protruding beyond the needle segment on all sides. The needles made of fentanyl citrate and Resomer R 202 are pierced through the horny layer in the process. Resomer R 202 breaks down, thereby releasing fentanyl citrate into the hypodermis tissue, from where it reaches the blood circulatory system with some delay.

EXAMPLE 2

5 g fentanyl citrate is extruded in 95 g polyvinyl alcohol above the glass transition temperature of the mixture of the two components by way of melt extrusion into a homogeneous strand, a so-called "extruded filament," suitable for the particular 3D printer, and then is wound to form a roll. This active ingredient polymer strand is melted using the 3D printer and brought into the shape of needles. This results in needles having a height of 0.5 to 1.0 mm. The room temperature and moisture are kept as low as possible so as to ensure that the curing process takes place as quickly as possible, and so as to prevent the hygroscopic polymer from absorbing water. The film is placed, with the side facing away from the needles, onto a film coated with contact adhesive, so that the adhesive film protrudes over the needle patch in the form of an "over-patch." The needle patch and the contact adhesive mesh are covered for storage with a thermoforming sheet made of siliconized HDPE film, 175 µm, so as to protect the polymer needles. For the delivery, the thermoformed film is pulled off. The needle patch is attached to a patient suffering from pain and fixed by way of the adhesive layer protruding beyond the needle segment on all sides. The needles made of fentanyl citrate and polyvinyl alcohol are pierced through the horny layer in the process. The polyvinyl alcohol dissolves, thereby releasing fentanyl citrate beneath the stratum corneum, from where it reaches the blood circulatory system.

EXAMPLE 3

5 g fentanyl citrate is heated in 95 g polyvinyl alcohol to a temperature above the melting temperature of the mixture, and the melted mixture is brought into the shape of needles by way of an injection molding process. This results in needles having a height of 0.5 to 1.0 mm. The room temperature and moisture are kept as low as possible so as to ensure that the curing process takes place as quickly as possible, and so as to prevent the hygroscopic polymer from absorbing water. The film is placed, with the side facing away from the needles, onto a film coated with contact adhesive, so that the adhesive film protrudes over the needle patch in the form of an "over-patch." The needle patch and the contact adhesive mesh are covered for storage with a thermoforming sheet made of siliconized HDPE film, 175 µm, so as to protect the polymer needles. For the delivery, the thermoformed film is pulled off. The needle patch is attached to a patient suffering from pain and fixed by way of the adhesive layer protruding beyond the needle segment on all sides. The needles made of fentanyl citrate and polyvinyl alcohol are pierced through the horny layer in the process. The polyvinyl alcohol dissolves, thereby releasing fentanyl citrate beneath the stratum corneum, from where it reaches the blood circulatory system.

EXAMPLE 4

7.5 g buprenorphine HCl is heated in 92.5 g polyvinyl alcohol to a temperature above the melting temperature of the mixture and extruded by way of a twin-screw extruder, and the resulting strand is printed by way of a 3D printing process in the form of needles onto a film that does not allow active ingredients to pass, resulting in needles having a height of 0.5 to 1.0 mm. The room temperature and moisture are kept as low as possible so as to ensure that the curing process takes place as quickly as possible, and so as to prevent the hygroscopic polymer from absorbing water. The film is placed, with the side facing away from the needles, onto a film coated with contact adhesive, so that the adhesive film protrudes over the needle patch in the form of an "over-patch." The needle patch and the contact adhesive mesh are covered for storage with a thermoforming sheet made of siliconized HDPE film, 175 µm, so as to protect the polymer needles. For the delivery, the thermoformed film is pulled off. The needle patch is attached to a patient suffering from pain and fixed by way of the adhesive layer protruding beyond the needle segment on all sides. The needles made of buprenorphine HCl and polyvinyl alcohol are pierced through the horny layer in the process. The polyvinyl alcohol dissolves, thereby releasing buprenorphine HCl beneath the stratum corneum, from where it reaches the blood circulatory system.

EXAMPLE 5

5 g buprenorphine HCl is dissolved in 25 g of a 30% ethanolic solution made of polyvinylpyrrolidone K30, and is metered into a matrix comprising negative depressions for a needle array of, for example, 64 needles having a length of approximately 0.8 mm and a width of approximately 0.2 mm, at needle spacing of approximately 0.3 mm A recess is present thereabove for an array plate having a height of approximately 0.2 mm and a surface area of 1 cm$^2$. After the solvent has been removed by drying, an active ingredient-free base plate, made of a 30% methanolic solution made of PVPVA64, is metered over the needles so as to create an easy-to-bend plate, which also combines the needles to form a unit. The film is placed, with the side facing away from the needles, onto a film coated with contact adhesive, so that the adhesive film protrudes over the needle patch in the form of an "over-patch." The needle patch and the contact adhesive mesh are covered for storage with a thermoforming sheet made of siliconized HDPE film, 175 µm, so as to protect the polymer needles. For the delivery, the thermoformed film is pulled off. The needle patch is attached to a patient suffering from pain and fixed by way of the adhesive layer protruding beyond the needle segment on all sides. The needles made of buprenorphine HCl and polyvinylpyrrolidone are pierced through the horny layer in the process. The PVP K30 dissolves, thereby releasing buprenorphine HCl beneath the stratum corneum, from where it reaches the blood circulatory system.

The invention claimed is:

1. A microneedle array for use in the intradermal delivery of an analgesic in the form of a salt wherein a plurality of dissolvable microneedles are arranged on a carrier, characterized in that the microneedle array is applied by way of an applicator system, the applicator system comprising a trigger device, and the microneedles are composed of a formulation consisting of buprenorphine hydrochloride, and at least one water-soluble polymer wherein the buprenorphine hydrochloride is mixed in the polymer, and wherein the water-soluble polymer is selected from the group consisting of polyvinylpyrrolidone and polyvinyl alcohols.

2. The microneedle array for use with the intradermal delivery of an analgesic in the form of a salt according to claim 1, characterized in that the applicator system comprises a trigger device comprising a plunger, a push button or a thread.

3. A microneedle array for use with intradermal delivery according to claim 1, characterized in that the microneedle array is planar.

4. A microneedle array for use with intradermal delivery according to claim 1, characterized in that the density of the microneedles on a carrier is 5 to 5,000 pieces/cm$^2$.

5. A microneedle array for use according to claim 1, characterized in that the microneedle array comprises a fixation means that attaches the microneedle array to the skin of a patient or a test subject by the way of an adhesive strip, a patch, a band, rubber or a strap.

6. The applicator system comprising a microneedle array for use with intradermal delivery according to claim 3, characterized in that the trigger mechanism comprises a plunger, a push button or a thread.

7. The applicator system comprising a microneedle array for use with intradermal delivery according to claim 1, characterized in that the trigger mechanism is electrically or mechanically controlled.

8. A microneedle array for use in the intradermal delivery of an analgesic in the form of a salt, wherein a plurality of dissolvable microneedles are arranged on a carrier, characterized in that the microneedle array is applied by way of an applicator system, the applicator system comprising a trigger device which is electrically controlled, and the microneedles are composed of a formulation consisting of buprenorphine hydrochlorde, and at least one water-soluble polymer, and wherein the water-soluble polymer is selected from the group consisting of polyvinylpyrrolidone and polyvinyl alcohols.

9. A microneedle array for use in the intradermal delivery of an analgesic in the form of a salt, wherein a plurality of microneedles are arranged on a carrier, characterized in that the microneedle array is applied by way of an applicator system, the applicator system comprising a trigger device, and the microneedles are composed of a formulation consisting of buprenorphine hydrochloride, and at least one water-soluble polymer selected from the group consisting of polyvinylpyrrolidone and polyvinyl alcohols and wherein the microneedles are configured in a helical shape and can be rotatably disposed and thereby, when a rotating motion is applied, facilitate the penetration into the skin and effectuate anchoring in the skin, and wherein the analgesic salt is buprenorphine hydrochloride.

10. The microneedle array for use with intradermal delivery according to claim 1, wherein the microneedles are barbed hooks.

11. The microneedle array for use with intradermal delivery according to claim 1, wherein the microneedles are not hollow.

12. The microneedle array for use with intradermal delivery according to claim 1, wherein when the microneedles penetrate the skin the penetrated microneedles dissolve in-situ and directly resorb in the skin.

13. The microneedle array for use with intradermal delivery according to claim 1, wherein the buprenorphine hydrochloride is dissolved in the at least one water-soluble polymer.

14. The microneedle array for use with intradermal delivery according to claim 1, wherein the buprenorphine hydrochloride and the at least one water-soluble polymer are heated and extruded to form the microneedle.

15. The microneedle array for use with intradermal delivery according to claim 12, wherein the microneedles are not hollow and 1 part of the salt dissolves in 10 to 30 parts of the solvent and the polymers that dissolve up to 50% in water or ethanol or alcohol/water mixtures at room temperature, or up to 80% in boiling heat, that is, at approximately 78° C.

* * * * *